US006242620B1

(12) United States Patent
Elsasser et al.

(10) Patent No.: US 6,242,620 B1
(45) Date of Patent: Jun. 5, 2001

(54) PROCESS FOR MAKING CARBOXYLIC ACID ESTERS

(75) Inventors: A. Fred Elsasser, Cincinnati, OH (US); C. William Blewett, Fort Mitchell, KY (US); Charles M. White, Cincinnati, OH (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/035,681

(22) Filed: Mar. 5, 1998

(51) Int. Cl.[7] .......................................... C11C 3/00
(52) U.S. Cl. ........................ 554/170; 554/191; 554/195; 568/903; 568/913; 560/265
(58) Field of Search .................................. 554/195, 191, 554/170; 568/902, 913; 566/265

(56) References Cited

U.S. PATENT DOCUMENTS

| 5,180,858 | 1/1993 | Fleckenstein et al. | 568/885 |
| 5,302,748 | 4/1994 | Krbechek | 560/265 |

OTHER PUBLICATIONS

Chem. Abstr., vol. 104, No. 24, Jun. 16, 1986 (Columbus, OH), p. 105, col. 2, Abstract No. 209171s, Moy et al., "Vapor Phrase Hydrogenation of Carboxylic Acids to Esters and Alcohols".

Chem. Abstr., vol. 121, No. 6, Aug. 8, 1994 (Columbus, OH), p. 564, col. 1, Abstract No. 60253m, Wangemann et al., "Esters of Fatty Acids and Alkoxylated Alcohols as Antifoaming Agents".

Chem. Abstr., vol. 125, No. 19, Nov. 17, 1996 (Columbus, OH), p. 1090, col. 1, Abstract No. 247205x, Hara et al., "Hydrogenation of Carboxylic Acid Esters for Preparation of Alcohols".

Chem. Abstr., vol. 126, No. 5, Feb. 03, 1997 (Columbus, OH), p. 824, col. 1, Abstract No. 62488u, Guegan et al., "Purification of Synthetic Acid Esters Used as Oils for Refrigeration Machines".

*Primary Examiner*—Deborah D. Carr
(74) *Attorney, Agent, or Firm*—John E. Drach

(57) ABSTRACT

Sulfur and soap contaminants are removed from carboxylic acid esters by a process comprising the steps of: (1) contacting a carboxylic acid ester with an aqueous base at a temperature of from about 225° F. to about 280° F. while removing water to form a dry, crude ester; (2) contacting the dry, crude ester with an absorbent selected from the group consisting of silica gel, hydro-silica gel and mixtures thereof; (3) separating the absorbent from the ester.

36 Claims, No Drawings

PROCESS FOR MAKING CARBOXYLIC ACID ESTERS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

Fatty alcohols, i.e., predominantly linear, monohydric primary alcohols containing at least 8 carbon atoms, are important raw materials for the production of a number of products, for example, emulsifiers or surfactants. Fatty alcohols can be manufactured by catalytic high-pressure hydrogenation of fatty acid esters, preferably methyl esters. Typically, distilled methyl esters are passed in liquid form, together with a large excess of hydrogen, over fixedly arranged copper-containing mixed oxide catalysts, such as copper/zinc catalysts for example, at temperatures above 200° C. and under pressures of around 250 to 300 bar. Fatty acid esters are used instead of fatty acids in order to protect the catalysts against attack by the free carboxyl groups. The process is described in detail in U.S. Pat. No. 5,180,858, the entire contents of which are incorporated herein by reference.

Carboxylic acid esters suitable for conversion to the corresponding alcohols via catalytic hydrogenation must contain little or no sulfur-containing compounds or metallic soaps such as sodium, potassium, and calcium in order not to poison the hydrogenation catalyst. Carboxylic acid esters, particularly fatty acid methyl esters used in the production of alcohols such as fatty alcohols prepared from the corresponding carboxylic acid and an alcohol using a sulfur-containing catalyst such as para-toluene sulfonic acid and subsequently treated with a base such as KOH to remove harmful and unwanted contaminants are particularly susceptible to sulfur- and soap contamination. In order to be able to use these esters for hydrogenation to the corresponding alcohols, the ester would have to at least be washed with water or, more typically, distilled to bring the amount of sulfur-containing compounds and soaps to acceptable levels.

SUMMARY OF THE INVENTION

In its broadest aspect, the invention relates to a process for removing sulfur and soap contaminants from carboxylic acid esters. This process comprises contacting a carboxylic acid ester with an aqueous base such as aqueous potassium or sodium hydroxide at a temperature of from about 225° F. to about 280° F. Any water present is then removed and the dried crude ester is contacted with an absorbent such as silica gel or hydro-silica gel. The absorbent is then removed and the resulting purified ester contains little or no detectable sulfur and/or soap contamination.

Another aspect of the present invention relates to a process for making carboxylic acid esters containing little or no detectable sulfur and/or soap contamination. This process is particularly useful in instances where there are sulfur-containing contaminants present in the ester such as when a sulfur-containing catalyst is used in a direct esterification reaction. For example, when a carboxylic acid such as a fatty acid and a low molecular weight alcohol such as $C_{1-4}$ alkanol are reacted in the presence of a sulfur-containing acid catalyst such as para-toluene sulfonic acid, the crude ester thus formed may contain sulfur contaminants. After the reaction has been completed, the crude ester is heated in the presence of an aqueous base such as aqueous sodium or potassium hydroxide to a temperature of from about 225° F. to about 280° F. Any water present is then removed and the dried crude ester is then slurried with an absorbent such as silica gel or hydro-silica gel. The absorbent is then removed.

Yet another aspect of the invention relates to a method of making alcohols using carboxylic acid esters prepared as described above. The method comprises contacting a carboxylic acid ester with hydrogen at a temperature of from about 200 to about 250° C. and under a pressure of from about 200 to about 250 bar in the presence of a catalyst-effective amount of a hydrogenation catalyst such as a copper-zinc catalyst as described in detail in U.S. Pat. No. 5,180,858.

BRIEF DESCRIPTION OF THE SEVERAL VIEWS OF THE DRAWING

Not Applicable.

DETAILED DESCRIPTION OF THE INVENTION

For purposes of this invention, the term carboxylic acid includes mono- and dicarboxylic acids. The term soap refers to metallic salts of fatty acids having from 6 to 36 carbon atoms such as the sodium, potassium, and calcium salts.

According to one aspect of the present invention, sulfur and soap contaminants can be removed from a carboxylic acid ester by contacting the ester with an aqueous base such as aqueous sodium or potassium hydroxide at a temperature of from about 225° F. to about 280° F. Any water present is removed simultaneously and the dried crude ester is then contacted with an absorbent such as silica gel or hydro-silica gel. The absorbent is then removed and the resulting ester contains little or no detectable sulfur and/or soap contamination. The amount of soap in an ester is reflected in the metal content which can be determined by atomic absorption spectroscopy. The type of soap contamination in an ester will depend upon the nature of the base used to treat the crude ester in the first step of the process according to the invention. Therefore, for example, if KOH is used, potassium soaps will be the contaminant in the purified ester and the amount of soap will be reflected by the amount of potassium. If NaOH is used, sodium soaps will be the contaminant and the amount of soap will be reflected by the amount of sodium.

The first step of the process comprises contacting a carboxylic acid ester with an aqueous base at a temperature of from about 225° F. to about 280° F. Any carboxylic acid ester can be used in the process according to the invention. Any ester made by reacting a saturated or unsaturated aliphatic carboxylic acid, a saturated or unsaturated aliphatic dicarboxylic acid, an aromatic carboxylic acid or an aromatic dicarboxylic acid with a saturated or unsaturated aliphatic alcohol or aromatic alcohol can be used. The process is most useful in the preparation of alkyl esters of saturated and unsaturated carboxylic acids having from 6 to 36 carbon atoms and mixtures of such saturated and unsaturated carboxylic acids. While the alkyl portion of the ester can be any alkyl group having from 1 to 22 carbon atoms, the preferred alkyl groups are those having from 1 to 4 carbon atoms. Thus, the preferred esters are methyl, ethyl, n-propyl, iso-propyl, n-butyl, sec-butyl, and tert-butyl esters of saturated and unsaturated carboxylic acids having from 6 to 36 carbon atoms. The process is particularly applicable to methyl esters of fatty acids such as methyl oleate, methyl isostearate or the dimethyl ester of $C_{36}$ dimer acid which are subsequently converted to the corresponding fatty alcohols by catalytic hydrogenation since these esters must contain a minimum of sulfur-containing compounds and soaps which, if present, are highly likely to poison the hydrogenation catalyst.

The base present in the aqueous base solution can be any alkali metal hydroxide or alkaline earth metal hydroxide such as KOH, NaOH, Ca(OH)$_2$, and the like. Preferred bases are NaOH and KOH with the most preferred being KOH. The most preferred aqueous base is 45% aqueous KOH. The amount of the base can be in the range of from about 0.05% to about 0.25% of active or dry base based on the weight of ester.

The aqueous base is mixed with the ester beginning at ambient temperature and the mixture is heated to a temperature of from about 225° F. to about 280° F. with the preferred range being from 225° F. to about 235° F. The time that the mixture remains in the temperature range of from about 225° F. to about 280° F. is not critical as long as the mixture achieves a temperature of at least 225° F. During the heat-up period, most of any water present is removed via distillation. The pressure above the mixture can be decreased, if desired, to facilitate the water removal. The dried ester is cooled to a temperature of less than about 200° F. and then contacted with an absorbent such as silica gel or hydro-silica gel. Typically, the hot, dried ester is stirred together with the absorbent. The absorbent can remain in contact with the ester for a time period of up to about one hour. The minimum contact time will vary depending upon the particular ester used and can be easily determined by one of ordinary skill in the art. The typical contact time will be from about 5 minutes to about 1 hour. The amount of the absorbent can range from 0.5% to about 1.0% by weight of the hot, dried ester. Preferably, the amount of absorbent will be in the range of from 0.75% to about 1.0% by weight of the hot, dried ester. Preferred absorbents are silica gel and hydro-silica gel and mixtures thereof with the most preferred absorbent being hydro-silica gel. Hydro-silica gel is available commercially as, for example, SORBSIL® R40 and SORBSIL® R92, trademark products of Crosfield Company, Joliet, Ill. and TRISYL®, TRISYL® 627 and TRISYL® 300, trademark products of W.R. Grace & Co., Baltimore, Md.

The absorbent is then removed by any separation means such as by filtration. The resulting ester contains little or no detectable sulfur and/or soap contamination as measured by Inductively Coupled Plasma Spectroscopy and Atomic Absorption Spectroscopy respectively. If potassium soaps are contaminants, the amount of potassium in the purified ester should be less than 10 ppm and preferably less than 2 ppm. The amount of sulfur in the purified ester should be less than 20 ppm and preferably less than 10 ppm.

In the aspect of the invention relating to a process for making carboxylic acids, a carboxylic acid is reacted with an alcohol in the presence of a catalyst-effective amount of sulfuric acid or an aliphatic or an aromatic sulfonic acid catalyst forming a crude ester containing sulfur contaminants. Preferred sulfonic acid catalysts are para-toluene sulfonic acid, methyl sulfonic acid, an alkyl benzene sulfonic acid and a sulfonated polystyrene resin. A catalyst-effective amount is any amount necessary to produce an ester in a specified time, in a specified yield, and/or to a specified acid number and is readily determinable by those skilled in the art. The amount of catalyst that can be used can be from about 0.05% to about 0.3% and will typically vary from about 0.075% to about 0.1%. The crude ester is then treated as described herein. The types of carboxylic acids that can be used in the process according to the invention are disclosed herein. Any aliphatic or aromatic alcohol can be used in the process according to the invention. The process according to the invention is particularly applicable to the preparation of $C_{1-4}$ alkyl esters of fatty acids. Thus, $C_{1-4}$ alkanols are reacted in the presence of a sulfur-containing acid catalyst such as those disclosed herein.

In the aspect of the invention pertaining to the preparation of an alcohol, an ester of a carboxylic acid is contacted with hydrogen at a temperature of from about 200 to about 250° C. and under a pressure of from about 200 to about 250 bar in the presence of a catalyst-effective amount of a hydrogenation catalyst. A catalyst-effective amount is any amount necessary to convert a carboxylic acid ester to the corresponding alcohol under a given set of process variables such as time, temperature and pressure. The process is described in detail in U.S. Pat. No. 5,180,858. The process for making alcohols is particularly applicable to the manufacture of fatty alcohols by hydrogenation of a $C_{1-4}$ alkyl ester of a fatty acid in the presence of a catalyst-effective amount of a copper-containing catalyst, preferably a copper-zinc catalyst.

The following examples are meant to illustrate but not to limit the invention.

EXAMPLE 1

Preparation of Methyl Isostearate

About 780 grams of isostearic acid (acid number=194.4), 1 gram of p-toluenesulfonic acid were charged to a flask equipped with a heating mantle, stirrer, sub-surface inlet tube with a nitrogen purge and a condenser. The contents of the flask were heated under nitrogen flow to 117° C. About 400 grams of methanol were then added via the sub-surface inlet tube over 3.5 hours (acid number=9.6), 200 grams of additional methanol were added and the reaction continued for another 1.5 hours to obtain a final acid number of 0.6.

EXAMPLE 2

Treatment of Methyl Oleate

About 200 grams of production grade crude methyl oleate pretreated with 45% aqueous KOH (35 lbs of 45% aq. KOH per 30,000 lbs of methyl oleate) was heated to 120° C. (about 248° F.) and held for one hour. The heat source was removed and 2 grams of SORBSIL® R92 and 0.5 grams of bleaching clay (for color development) were added at a temperature of 90° C. (about 194° F.). The contents of the flask were stirred together for about 15 minutes during which time the temperature fell to about 60° C. at which point 0.25 grams of Dicalite filter aid was added. The slurry was filtered through #1 Whatman filter paper in a Buchner funnel. The product contained less than 2 ppm potassium and 6 ppm sulfur.

What is claimed is:

1. A process for treating a carboxylic acid ester comprising the steps of: (1) contacting a carboxylic acid ester with an aqueous base at a temperature of from about 225° F. to about 280° F. while removing water to form a dry, crude ester; (2) contacting the dry, crude ester with an absorbent selected from the group consisting of silica gel, hydro-silica gel and mixtures thereof; (3) separating the absorbent from the ester.

2. The process of claim 1 wherein step (1) is carried out at a temperature of from about 225° F. to about 235° F.

3. The process of claim 1 wherein step (2) is carried out at a temperature of less than about 200° F.

4. The process of claim 1 wherein the base is KOH, NaOH, Ca(OH)$_2$ or mixtures thereof.

5. The process of claim 4 wherein the aqueous base is a 45% aqueous KOH solution.

6. The process of claim 1 wherein the amount of the base is from about 0.05% to about 0.25% of dry base based on the weight of the ester.

7. The process of claim 1 wherein the ester is methyl oleate, methyl isostearate or the dimethyl ester of $C_{36}$ dimer acid.

8. A process for treating methyl isostearate comprising the steps of: (1) contacting methyl isostearate with aqueous KOH at a temperature of from about 225° F. to about 280° F. while removing water to form dry, crude methyl isostearate; (2) contacting the dry, crude methyl isostearate with an absorbent selected from the group consisting of silica gel, hydro-silica gel and mixtures thereof; (3) separating the absorbent from the methyl isostearate.

9. The process of claim 8 wherein step (1) is carried out at a temperature of from about 225° F. to about 235° F.

10. The process of claim 8 wherein step (2) is carried out at a temperature of less than about 200° F.

11. The process of claim 8 wherein the aqueous base is a 45% aqueous KOH solution.

12. A process for making a carboxylic acid ester comprising the steps of: (1) reacting a carboxylic acid and an alcohol in the presence of a catalyst-effective amount of a sulfur-containing catalyst selected from the group consisting of sulfuric acid, an aliphatic sulfonic acid, an aromatic sulfonic acid and mixtures thereof to form an ester; (2) contacting the ester with an aqueous base at a temperature of from about 225° F. to about 280° F. while removing water to form a dry, crude ester; (3) contacting the dry, crude ester with an absorbent selected from the group consisting of silica gel, hydro-silica gel and mixtures thereof; (3) separating the absorbent from the ester.

13. The process of claim 12 wherein the temperature in step (2) is from about 225° F. to about 235° F.

14. The process of claim 12 wherein step (3) is carried out at a temperature of less than about 200° F.

15. The process of claim 12 wherein the base is KOH, NaOH, Ca(OH)$_2$ or mixtures thereof.

16. The process of claim 15 wherein the aqueous base is a 45% aqueous KOH solution.

17. The process of claim 12 wherein the amount of the base is from about 0.05% to about 0.25% of dry base based on the weight of the ester.

18. The process of claim 12 wherein the ester is methyl oleate, methyl isostearate or the dimethyl ester of $C_{36}$ dimer acid.

19. The process of claim 12 wherein the catalyst is para-toluene sulfonic acid, methyl sulfonic acid, an alkyl benzene sulfonic acid, a sulfonated polystyrene resin or a combination thereof.

20. The process of claim 19 wherein the catalyst is para-toluene sulfonic acid.

21. A process for making methyl isostearate comprising the steps of: (1) reacting isostearic acid and methanol in the presence of a catalyst-effective amount of a sulfur-containing catalyst selected from the group consisting of sulfuric acid, an aliphatic sulfonic acid, an aromatic sulfonic acid and mixtures thereof to form an ester; (2) contacting the ester with an aqueous base at a temperature of from about 225° F. to about 280° F. while removing water to form a dry, crude ester; (3) contacting the dry, crude ester with an absorbent selected from the group consisting of silica gel, hydro-silica gel and mixtures thereof; (3) separating the absorbent from the ester.

22. The process of claim 21 wherein the temperature in step (2) is from about 225° F. to about 235° F.

23. The process of claim 21 wherein step (3) is carried out at a temperature of less than about 200° F.

24. The process of claim 21 wherein the aqueous base is a 45% aqueous KOH solution.

25. The process of claim 21 wherein the catalyst is para-toluene sulfonic acid, methyl sulfonic acid, an alkyl benzene sulfonic acid, a sulfonated polystyrene resin or a combination thereof.

26. The process of claim 24 wherein the catalyst is para-toluene sulfonic acid.

27. A process for making an alcohol comprising the steps of: (1) reacting a carboxylic acid and an alcohol in the presence of a catalyst-effective amount of a sulfur-containing catalyst selected from the group consisting of sulfuric acid, an aliphatic sulfonic acid, an aromatic sulfonic acid and mixtures thereof to form an ester; (2) contacting the ester with an aqueous base at a temperature of from about 225° F. to about 280° F. while removing water to form a dry, crude ester; (3) contacting the dry, crude ester with an absorbent selected from the group consisting of silica gel, hydro-silica gel and mixtures thereof; (4) separating the absorbent from the ester; (5) contacting the ester with hydrogen at a temperature of from about 200 to about 250° C. and under a pressure of from about 200 to about 250 bar in the presence of a catalyst-effective amount of a hydrogenation catalyst.

28. The process of claim 27 wherein the carboxylic acid is isostearic acid and the alcohol is methanol.

29. The process of claim 27 wherein the temperature in step (2) is from about 225° F. to about 235° F.

30. The process of claim 27 wherein step (3) is carried out at a temperature of less than about 200° F.

31. The process of claim 27 wherein the base is KOH, NaOH, Ca(OH)$_2$ or mixtures thereof.

32. The process of claim 31 wherein the aqueous base is a 45% aqueous KOH solution.

33. The process of claim 27 wherein the amount of the base is from about 0.05% to about 0.25% of dry base based on the weight of the ester.

34. The process of claim 27 wherein the catalyst in step (5) is a copper-zinc catalyst.

35. The process of claim 27 wherein the catalyst in step (1) is para-toluene sulfonic acid, methyl sulfonic acid, an alkyl benzene sulfonic acid, a sulfonated polystyrene resin or a combination thereof.

36. The process of claim 35 wherein the catalyst is para-toluene sulfonic acid.

\* \* \* \* \*